United States Patent [19]
Adams et al.

[11] Patent Number: 4,854,724
[45] Date of Patent: * Aug. 8, 1989

[54] METHOD OF AND APPARATUS FOR THERMOGRAPHIC EVALUATION OF SPOT WELDS

[75] Inventors: Mark J. Adams, Kennesaw, Ga.; Elton M. Crisman, Jr., St. Cloud, Fla.

[73] Assignee: Lockheed Corporation, Calabasas, Calif.

[ * ] Notice: The portion of the term of this patent subsequent to Jul. 9, 2001 has been disclaimed.

[21] Appl. No.: 836,366

[22] Filed: Mar. 5, 1986

Related U.S. Application Data

[63] Continuation-in-part of Ser. No. 629,069, Jul. 9, 1984, Pat. No. 4,647,220.

[51] Int. Cl.[4] .................................................. G01N 25/72
[52] U.S. Cl. ........................................ 374/5; 374/124; 374/137
[58] Field of Search ................. 374/4, 5, 57, 124, 126, 374/137

[56] References Cited

U.S. PATENT DOCUMENTS

| | | | |
|---|---|---|---|
| 3,020,745 | 2/1962 | Sielicki | 374/5 |
| 3,427,861 | 2/1969 | Maley | 374/5 |
| 3,555,879 | 1/1971 | Schroeer et al. | 374/5 |
| 3,566,669 | 3/1971 | Lawrence et al. | 374/124 |
| 3,583,223 | 6/1971 | Olsson | 374/124 |
| 3,635,085 | 1/1972 | Shimotsuma et al. | 374/137 |
| 3,644,667 | 2/1972 | Shimotsuma et al. | 374/124 |
| 3,718,757 | 2/1973 | Gulitz et al. | 374/124 |
| 3,805,073 | 4/1974 | Jayachandra et al. | 374/4 |
| 4,083,223 | 4/1978 | Hashimoto et al. | 374/5 |

FOREIGN PATENT DOCUMENTS

| | | | |
|---|---|---|---|
| 0039433 | 4/1981 | Japan | 374/124 |
| 58-124938 | 7/1983 | Japan | 374/4 |
| 0089740 | 5/1985 | Japan | 374/4 |

OTHER PUBLICATIONS

Cross et al, E. F., "Measurement of Aircraft Surface Temperatures with an Infrared Television System," Proceedings of the SPIE 14th Annual Technical Symposium: Photo-Optical Instrumentation Application and Theory, San Francisco, Calif. U.S.A. (Aug. 11-14, 1969) pp. 59-65.

Primary Examiner—Charles Frankfort
Assistant Examiner—Thomas B. Will
Attorney, Agent, or Firm—Eric R. Katz; Stanley L. Tate

[57] ABSTRACT

A method of and apparatus for the non-destructive evaluation of welds joining metal bodies employing infrared thermography the method comprising the steps of applying thermal energy to a weld and observing temperature differentials that occur on the weld's surface. The apparatus comprises a device for applying thermal energy to welds being inspected; a device for scanning the weld surface for infrared radiation being emitted therefrom; a device for capturing the emitted radiation and converting it to a signal representative of the thermophysical characteristics of the weld; and a device for visually displaying the signal in a form suitable for interpretation.

19 Claims, 5 Drawing Sheets

METHOD OF AND APPARATUS FOR THERMOGRAPHIC EVALUATION OF SPOT WELDS

CROSS REFERENCE TO RELATED APPLICATIONS

This application is a continuation-in-part of copending application Ser. No. 629,069 filed July 9, 1984, now U.S. Pat. No. 4,647,220.

TECHNICAL FIELD

This invention generally relates to a method of and apparatus for non-destructive testing of welds and more particularly relates to a method of and apparatus for using infrared analysis to detect temperature differentials caused by the differences in the thermal conductivities of poor quality welds and good quality welds.

BACKGROUND ART

In any machine or structure there are numerous instances where permanent junctions between component parts are required. The use of welding in assembling metal structures and machines is thus very extensive in present day technology. Typical of such practice is the welding of joints in pipe lines eliminating flanges, couplings and cumbersome fittings. Bridges and buildings of structural steel are fabricated using arc welds to replace riveted connections. Shipbuilders use welding as a principal means of fabrication. Where weight reduction is as important as strength, welding is especially suitable because the weight of rivets and bolts as well as the flanges in which they are seated can be eliminated. To the above illustrations may be added aircraft and missile structures in which welding has now become a standard practice.

As used herein, welding shall mean a method of joining metals by means of fusion or solid state processes. Metals having similar composition may be united in one homogeneous piece by fusing together contacting edges or by adding a molten metal having appropriate metallurgical characteristics at a place where it will form a fused joint with each piece.

Currently accepted weld inspection procedures rely on visual observation and X-ray examination, X-ray inspection is time consuming and cannot provide real-time evaluation of welds being inspected and visual inspection methods fail to detect flawed welds on many occasions because techniques currently in use are very subjective and are highly operator dependent.

In the past, infrared techniques have been used to non-destructively inspect workpieces for internal defects and one such method was described in U.S. Pat. No. 3,504,524. The method described in U.S. Pat. No. 3,504,524 involves spraying the workpiece with a vinyl base carrier of a carbon pigment to form a surface having a constant and high emissivity in the infrared region. After application of the coating, the test surface is heated with a suitable source of radiant energy and the temperatures of successive spots on the test surface are determined by scanning the coated surface with a radiometer. Output from the radiometer is then transmitted to an oscilliscope or other display device where any flaws in the workpiece are displayed as an infrared picture. U.S. Pat. No. 3,504,524 is particularly concerned with controlling the emissivity of the test surface at a standard level by applying a coating to the test surface that has uniform radiating characteristics. An essential characteristic of the coating applied to the test surface is that it must be easily removed when the test is completed.

U.S. Pat. No. 3,020,745 also discloses the use of an infrared detector to test metal objects for flaws. In this method the area being inspected is heated by induced eddy currents which uniformly increase the temperature of the test surface when no flaws are present. If a flaw exists in the test piece the induced current is concentrated about the edges of it and a hot spot develops which is detected by an infrared detector. This method also requires that the test surface be covered with a thin homogeneous coating having a high emissivity. U.S. Pat. Nos. 4,037,473; 3,314,293; and 2,846,882 also disclose the use of infrared detectors to measure the temperature of a workpiece. Additionally, the use of infrared thermography as an inspection tool is discussed in "Trouble-shooting Products through Infrared Thermography" which appeared in the Nov. 10, 1983 issue of Machine Design This paper points out that thermography can be used to characterize a complete temperature field around a particular point of interest. It also points out that only surface temperatures can be measured by this technique and that accurate readings are hard to obtain from shiny surfaces.

DISCLOSURE OF THE INVENTION

Accordingly, it is an object of the present invention to provide a non-destructive test procedure to test welds which can be used with an assembled aircraft.

Another object of the present invention is to provide a spot weld inspection method and apparatus employing infrared thermographic techniques to detect any localized temperature differences on the surface of an aircraft being tested for weld integrity, thus indicating the presence of a faulty weld.

The principal feature of the present invention is the provision of a totally new approach to the inspection of welds in aircraft, aircraft components, structures, substructures and the like, such inspection is currently being accomplished in the art by destructive means, by X-ray or by visual inspection. In accordance with the present invention, a method and apparatus are provided for inspecting spot welds in aircraft, aircraft components, structures, substructures and the like. The method and apparatus of the present invention may also be used to inspect welds in non-aircraft structures with equal processes. The method uses infrared thermographic analyses and comprises the steps of heating welds and detecting variations in thermophysical properties of the welds being tested with thermographic imaging techniques.

Another feature of this invention is the provision of a video compatible infrared thermal imaging scanner for detecting variations as described. The scanner is a small, light-weight, portable field instrument that produces a television compatible video output signal representative of the thermophysical characteristics of the object it is viewing. The viewed scene is displayed on either a black and white or color monitor and may be recorded onto video tape for retention as a permanent record using a video cassette recorder or other suitable recording device.

In addition to the feature of video compatibility, the invention is further characterized by the simplicity and ease with which these welds are subjected to infrared radiation. In accordance with the present invention, infrared radiation is directed against the surface of the welds being inspected in pulses from an infrared lamp by, for example, combining the infrared lamp with a mechanical or electrical shutter mechanism so that the frequency and duration of the pulses will be known. The infrared radiation may also be pulsed using an electronic or other similar control mechanism that alternatively turns the power source on and then off at a specific frequency. The frequency and duration of the pulses are based upon the physical and chemical characteristics of the welds being evaluated. The pulsed radiation raises the temperature of the welds being evaluated to a temperature above their normal ambient. After the temperature of the welds has been raised above its ambient, flawed welds are detected as localized hot spots because the thermal conductivity of a good weld is higher than the thermal conductivity of a flawed weld.

Still another feature of the present invention is the ability of the scanner to be fitted with a variety of optical accessories including view expanding lenses, close up lenses, and telescopic lenses thus providing the capability of viewing a weld from a distance without the need of bringing the infrared scanner close to the inspection site.

Still another feature of the present invention is the provision of sighting means for visually indicating to the operator the particular area of an aircraft or other structure being evaluated that is being viewed by the scanner. In accordance with one embodiment of the present invention the sighting means takes the form of a hand-held pointer or more preferably, a laser mounted on the scanner to mark the test area being viewed by the scanner with a beam of light.

Another important feature of the present invention is the provision of an auto-focus, low light video camera which has a remote control zoom lens to provide the operator with a television-like display of the area being scanned.

A useful feature of the present invention is the remote control pan and tilt capability of the scanner.

Yet another feature of the present invention is the provision of contact heating apparatus which may be brought into physical contact with welds being evaluated on a surface of the welds which is on the opposite side of the surface being viewed by the scanner.

Still another important feature of the present invention is the provision of means to determine the intensity and distribution of heat transmission across the total area of a weld that is being evaluated. This allows incremental analysis of a weld thereby substantially eliminating the possibility of undetected flaws being hidden in an inspected weld.

Another feature of the present invention is the provision of a real-time thermal map of the image surface of the test piece.

Another feature of the present invention is the provision of means such as a video cassette recorder to record as a permanent record a thermal map of the welds in every aircraft inspected thereby creating history of each aircraft which can be used to predict future maintenance needs.

A very important feature of the present invention is the provision of line scan imaging capability. The ability to observe the thermal characteristics in distinctive form greatly ehances the sensitivity of the procedure thus making it possible to detect very small flaws in a weld,.

One advantage of the present invention is that this method can be applied to any metal in any configuration in either a coated or uncoated condition. While the inventors' use of this method has been primarily to test aircraft structures and substructures, the invention has broader applicability.

Another advantage of the present invention is that it eliminates the need for destructive testing and makes possible the inspection of 100 percent of the welds used in the construction of an aircraft.

In accordance with these and other objects, features and advantages of the present invention, there is provided a method of inspecting welds joining metal objects comprising the steps of heating the welds so that the temperature of the welds is raised above ambient; scanning the surface of the welds with a sensing device to detect and record any temperature differentials present on the surface of the welds; sensing any detected temperature differentials and producing an electrical signal representative of the intensity and location of such differentials; transmitting the signal to a video display apparatus and displaying the transmitted signal on the video display apparatus in the form of a thermal map of the test surface.

In accordance with the present invention the method further comprises the step of displaying the transmitted signal on a video display apparatus as a live scan of the inspection site so that the intensity of an observed temperature is objectively quantified.

In accordance with the present invention the method further comprises the step of providing a source of thermal energy; contacting welds individually with the source of thermal energy so that the temperatures of the welds are raised above ambient, with the duration of the contact between the welds and the source of thermal energy being relative to the thickness of the welds and the thermal conductivities of the metals being joined; and removing the thermal energy source from contact with the welds after the temperatures of the welds have been raised above ambient.

In accordance with the present invention the method also comprises the steps of: sensing the rates at which the welds cool after the thermal energy source is removed from contact therewith by means of a radiometer; converting the sensed rate of cooling into an electrical signal representative thereof; and transmitting the electrical signal to a video display apparatus.

Also in accordance with the present invention there is provided an emissivity independent method for inspecting welds joining metal objects comprising the steps of: providing a source of pulsating infrared radiation of a first wave length: directing pulses of infrared radiation from this source onto the surface of welds so that the temperatures of the welds are raised above ambient; scanning the surface of the welds with an infrared radiation detection device for infrared radiation of a second wave length which is being emitted from the welds so that any temperature differentials which might occur in the welds as a result of their exposure to the pulses of first wave length radiation may be detected and quantified; and converting detected temperature differentials into video signals and displaying the same on a video display apparatus in a form representative of the intensity of the differentials.

Further in accordance with the present invention, the method comprises the step of adapting the frequency and duration of the pulses of radiation to the thermal conductivity and thickness of the welds whereby heat is conducted away from the welds at a rate which is less than the rate at which radiant energy is applied to the welds.

Also in accordance with the present invention, the method comprises the step of adapting the frequency and duration of the pulses of radiation to the thermal conductivity and thickness of the welds whereby after the temperatures of the welds are raised above their normal ambient, heat is conducted away from the welds at a rate which is greater than the rate at which thermal energy is applied to the weld surface.

The present invention also comprises apparatus for the thermographic evaluation of welds which comprises heating means for heating welds so that the temperatures of the welds are raised above their normal ambient; scanning means for scanning the surfaces of the welds to detect and record any temperature differentials in the welds; sensing means to sense the detected temperature differentials and convert them into a signal representative of the intensity of the temperature differentials: transmission means for transmitting such signals to a video display and video display means for displaying a video image of the signal and comparing the temperature differentials against known standards.

In accordance with the present invention the heating means generally comprises an infrared source adapted to generate pulses of infrared radiation of a predetermined frequency and duration. The pulses of energy can either be produced by using an electronic or mechanical shutter mechanism or either an electronic or mechanical means to interrupt the flow of power to the infrared source.

In accordance with the present invention the heating means generally comprises a contact heat source adapted generate pulses of infrared radiation of a predetermined frequency and duration. The pulses of energy can either be produced by using an electronic or mechanical shutter mechanism or either an electronic or mechanical means to interrupt the flow of power to the infrared source.

In accordance with the present invention the heating means generally comprises a contact heat source adapted to contact each weld in sequence on one side thereof. This requires no sophisticated shutter or power control equipment and permits an inspector to heat one side of a weld while imaging the other side of the object being tested.

Additionally, in accordance with the present invention the heating means comprises a laser adapted to heat each weld to a temperature above ambient by directing concentrated light energy onto each weld being inspected. The light energy is best applied in pulses of predetermined frequency and duration with the pulses being produced either by a mechanical or electronic shutter or by either a mechanical or electronic means for either mechanically or electrically interrupting the power to the laser.

Further, in accordance with the present invention, the scanning means comprises a scanning camera capable of detecting and capturing infrared radiation within a specific wave length band. The camera also includes an electro-optical transducer for converting the captured radiation into an electrical signal representative of the intensity of the captured radiation. The camera is also coupled with an infrared signal processor which converts the electrical signal into a video signal representative of the thermophysical characteristics of welds being imaged.

Additionally, in accordance with the present invention, the signal produced by the infrared signal processor is displayed either as a thermal map of the image surface or as a line scan and in a color form representative of the intensity of the radiation emitted by the welds being inspected. The monitor used to display the image may either be color or black and white, however, the video display when produced in color provides a more distinctive and a more easily interpreted representation of the thermophysical characteristics of the welds being inspected. The signal may also be recorded on video tape or similar medium if a permanent record is desired. When color processing is used, color enhancement electronics are provided to allow an operator to continuously observe temperature zones within the scene displayed. When this technique is used, each color represents a different isotherm range.

Also in accordance with the present invention, the infrared generator (source) is adapted to allow the operator to vary the intensity of the radiation being directed onto the welds being evaluated.

The apparatus of the present invention further comprises a sighting means for visually marking the weld that is being viewed by the scanning camera. The sighting means preferably takes the form of a laser mounted on the scanning camera so that the weld being viewed by the scanning camera is illuminated by a beam of light.

These and other objects, features and advantages of the present invention will become more readily apparent as the description proceeds with the following more detailed description of the preferred embodiment of the present invention, the apparatus portions of which are illustrated in the accompanying drawings. The drawings in which like reference characters indicate corresponding parts in all views, are not necessarily to scale, emphasis instead being placed on illustrating the principles of the invention.

BEST MODE OF CARRYING OUT THE INVENTION

Figure 1:
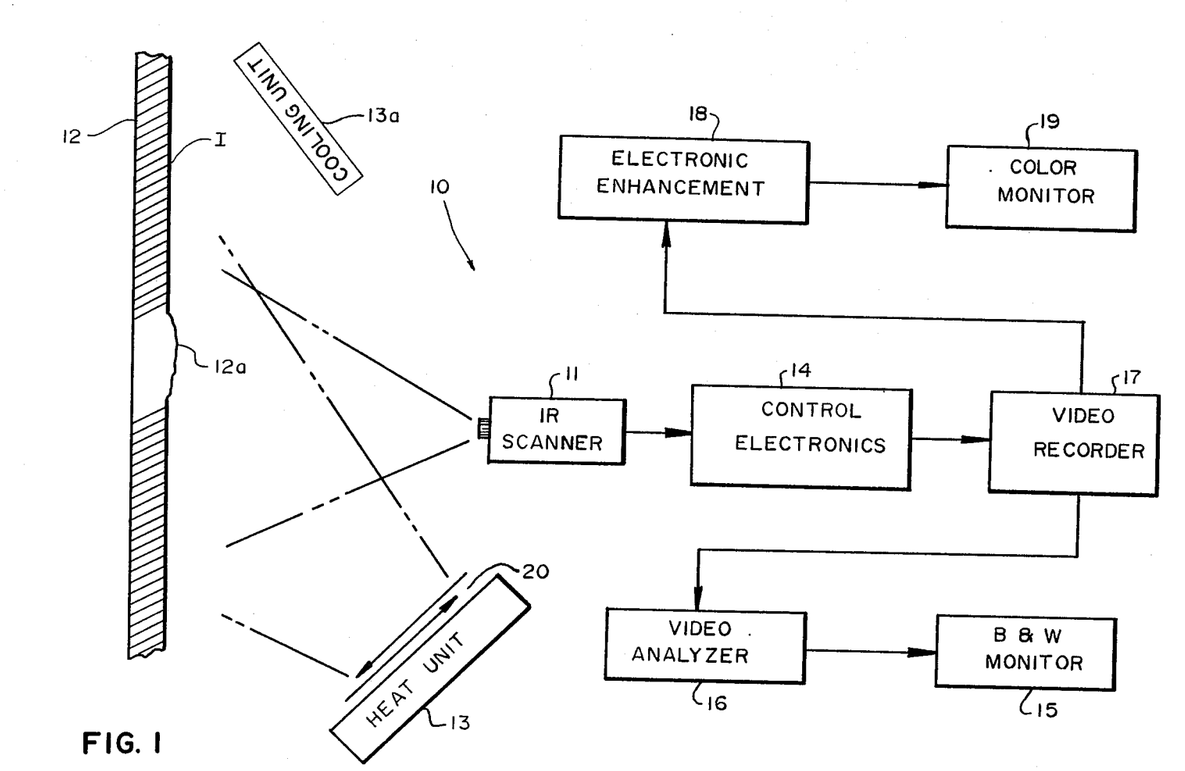
FIG. 1 is a schematic representation of the apparatus of the present invention including a stylized cross-sectional representation of a weld specimen.

Referring to FIG. 1, the apparatus of the present invention, generally indicated by the numeral 10, is illustrated in block diagram form in relation to a stylized partial cross-section of a weld specimen 12. In its simplest form, the apparatus 10 comprises a high resolution infrared scanner 11 which captures infrared radiation emitted from the image side I of the irradiated weld specimen 12. Infrared radiation is emitted from specimen 12 because the temperature of the weld 12a has been raised above its normal ambient by application of thermal energy from heat unit 13. The thermal energy from heat unit 13 is applied to specimen 12 as pulses of electromagnetic energy by means of an optical shutter mechanism or electronic pulsating means 20 so that any flaws in weld 12a can be visually characterized without resorting to destructive test procedures. As weld 12a heats to a temperature above its normal ambient it emits infrared radiation representative of its thermophysical characteristics. When this infrared radiation is captured by scanner 11 it is converted to a video compatible signal that is transmitted from the control-electronics unit 14 for display on a black and white monitor 15. Also included is a video cassette recorder (VCR) 17 for recording, for permanent retention, the image created from the infrared radiation capture by scanner 11. As will be explained in more detail hereinafter, the output of VCR 17, is inputted, for example, to video analyzer 16 of the type manufactured by Interactive Video Corporation which permits a pictel by pictel analysis of the image with a sensitivity of approximately 0.02° C. for display on black and white monitor 15. The output of VCR 17 is also inputted, for example, to an electronic enhancement arrangement 18 for color enhancement of the signal for display on color monitor 19. Scanner 11, which comprises, for example, a Model 525 Infrared Thermal Imaging Scanner produced by Inframetics, Inc., 25 Wiggins Avenue, Bedford, Mass. 01730, utilizes two low inertia mirrors to scan the image side I of the specimen 12 at television rates. An infrared detector, for example, a liquid nitrogen cooled mercury cadmium telluride HgCd+Te detector, converts naturally emited infrared radiation to an electrical signal which is employed to construct a television picture of the temperature pattern of the image side I of specimen 12 by means of the control-electronic unit 14 with a sensitivity of about ±0.2° C.

Figure 3:
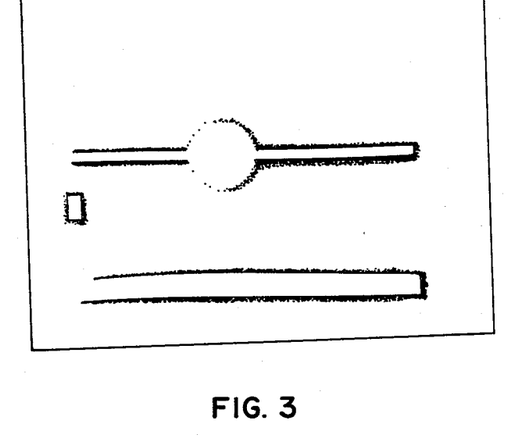
FIG. 3 is a photograph showing the thermal characteristics of a weld evaluated by the method of the present invention.
Figure 4:
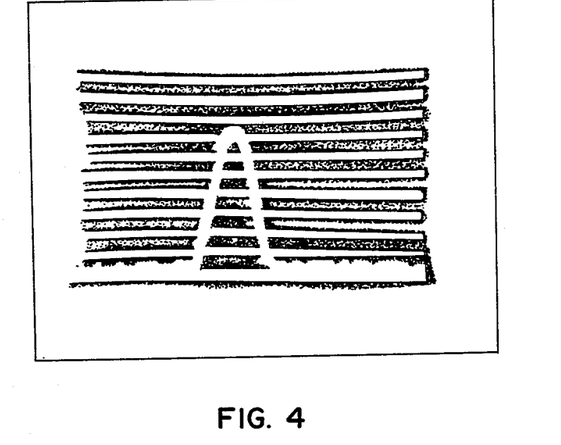
FIG. 4 is a photograph of the thermal characteristics of the weld pictured in FIG. 3 shown in scalar format.

Control-electronics unit 14 provides the basic display functions of the system. The image, FIG. 3, can be displayed as a normal television picture with the brightness and the tone of the displayed pattern indicating temperature difference in accordance with a calibrated gray scale. Alternatively, constant temperature contours are intensified over the normal image for selected temperatures, with a marker on the left of the display indicating the temperature differential as a fraction of the temperature range. The data can also be displayed with a brightness line indicating the vertical position of a continuous, horizontal scan wherein the temperature versus horizontal position is displayed for a continuous horizontal scan fixed in the image vertically by the brightness line, FIG. 4. When a display of this type is used the intensity of the emitted radiation is easily discernable. Additionally, colorizing can be added to the normal image display as will be described in more detail hereinafter, thus allowing an operator to continuously observe temperature zones within the image. When colorizing is used, each color represents a different isotherm range.

Figure 5:
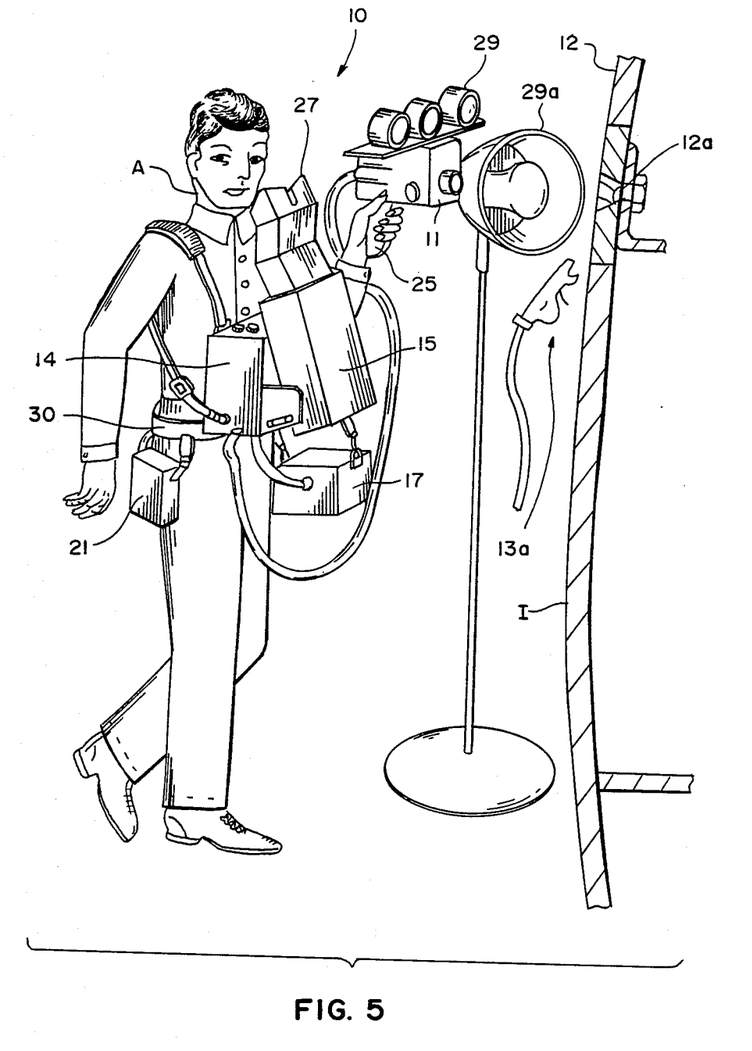
FIG. 5 is a perspective view illustrating the method and apparatus of the present invention in a portable configuration.

FIG. 5 shows the apparatus 10 in a portable configuration. In this configuration the apparatus 10 is carried by operator A by means of harness set 30. Battery 21 is provided to power apparatus 11 having a handle 25 for easy portability. A video cassette recorder (VCR) 17 records, for permanent retention, the image enacted from the infrared radiation captured by scanner 11. A viewing head 27, for monitor 15, is provided as well as camera adapter (not shown) for attaching a photographic camera to monitor 15 thereby permitting the photographing of the image displayed on monitor 15.

Apparatus 10 further comprises a source of infrared radiation 29 for directing infrared radiation onto specimen 12, for example, portions of an aircraft fuselage, to be inspected for weld integrity. In the embodiment represented by FIG. 5, the source of infrared radiation 29 is a bank of lights emitting radiation in the 0.5 to 2.5 micron wave length band. These lights are used to directly irradiate the image side I of the weld specimen 12 thereby raising the temperature of the weld 12a above its normal ambient. Radiation is applied to specimen 12 in pulses or bursts at a frequency and of a duration which are related to the thickness and thermal conductivity of the weld in such a way that temperature differentials occur because of the difference in the rates at which heat is transmitted through and away from sound and unsound welds. This occurs because sound welds will conduct heat more readily than unsound disbonded and highly porous welds. Even greater constrast can be achieved by using cooling unit 13a to cool the areas of specimen 12 that surround weld 12a thereby creating a heat sink and intensifying the perceived temperature build-up at the weld 12a. Best results have been achieved using the method and apparatus of the present invention with materials that are from about 0.016 to about 0.020 inches thick.

Returning now to FIG. 1, the method of the present invention will be explained in more detail. As shown in FIG. 1, the method comprises the steps of irradiating the image surface of specimen 12 with infrared radiation from the band having a wave length of from about 0.5 to about 2.5 microns in pulses or bursts until the temperature of the specimen 12 is above its normal ambient. By applying the infrared radiation in pulses which are relative to the thickness and thermal conductivity of specimen 12 temperature differentials are set up across the face of specimen 12 because a sound weld will conduct heat at a higher rate than a poor weld which is disbonded or porous. Simultaneous with the application of radiation to surface I, scanner 11 is used to view surface I and capture infrared radiation emitted therefrom. Scanner 11 is adapted to capture radiation in the 8 to 12 micron wavelength of the electromagnetic specimen and is blind to the radiation being used to heat surface I thereby making the method of the present invention substantially emissivity independent because scanner 11 will not pick up background or reflected radiation The radiation captured by scanner 11 is representative of the thermophysical characteristics of weld 12a and can be converted into a video compatible signal by control electronics 14 and displayed on monitors 15 as a thermograph of the specimen surface. When the areas of specimen 12 which surround a weld being tested are cooled as with 37 cooling unit 13a, more constrast is achieved. Interpretation of such thermograph allows the operator A, FIG. 5 to determine exactly the integrity of welds being evaluated. It is generally accepted within the infrared art that when temperatures below 1000° C. are being observed more photons of energy are available in the 8 to 12 micron wave length portion of the spectrum, therefore the sensitivity of the method is increased by locating the scanning band in that portion of the spectrum that has the most detectable radiation for the temperatures being observed. The 0.5 to 2.5 micron band was then chosen as the irradiating or heating band because of the desire to make the method emissivity independent.

Figure 2:
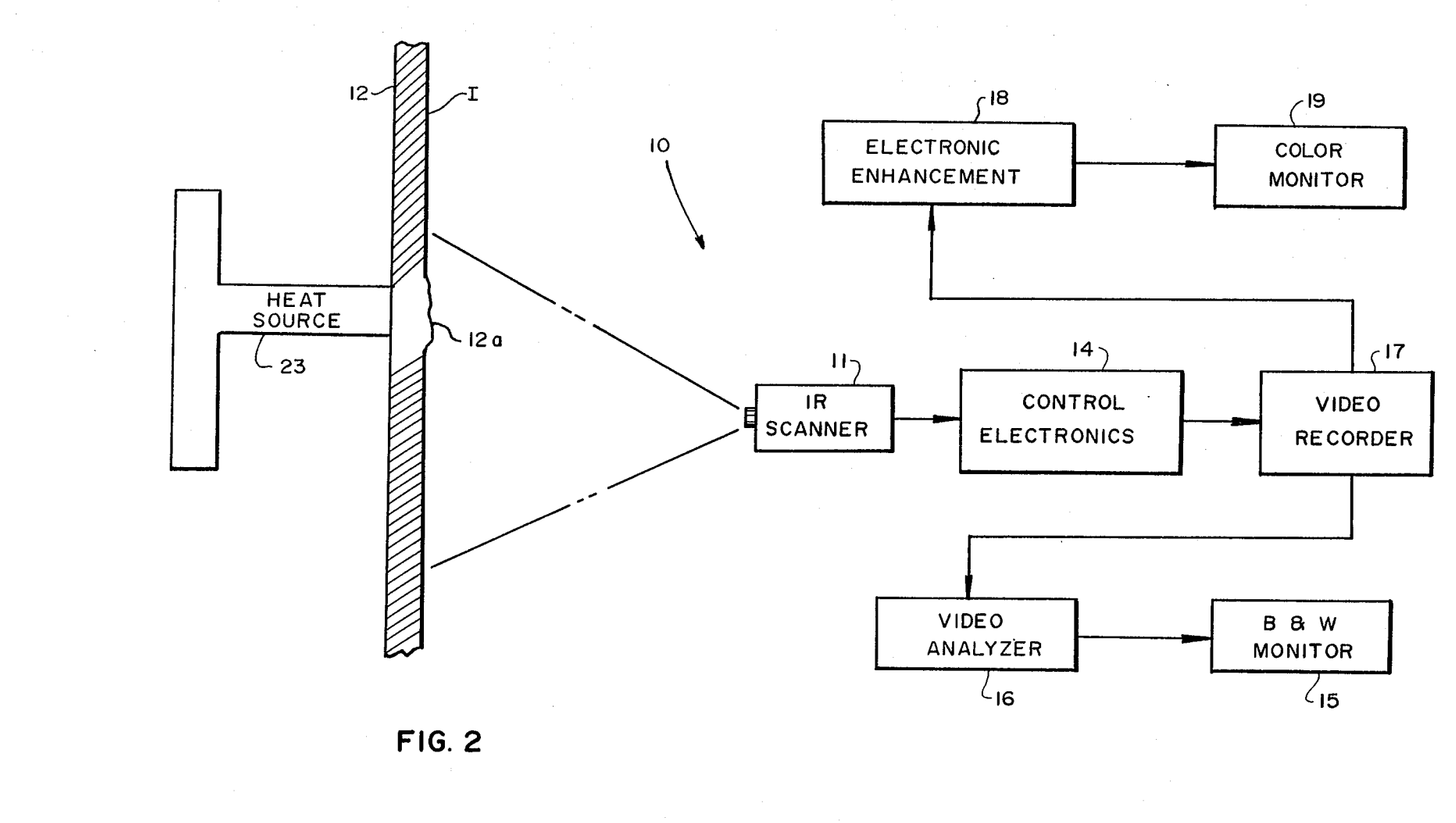
FIG. 2 is a schematic representation of an alternate embodiment of the apparatus of the present invention including a stylized cross-sectional representation of a weld specimen.

FIG. 2 illustrates another embodiment of the apparatus of the present invention. In this embodiment weld specimen 12a is heated to a temperature above its normal ambient by direct contact between heat source 23 and the weld. The heat unit 23 is brought into direct contact with weld 12a on the side away from IR scanner 11 so that when its temperature is raised above its normal ambient and infrared radiation begins to be emitted from weld 12a scanner 11 can be focused directly on weld 12a and the line of sight between weld 12a and scanner 11 is not interrupted. When this procedure is used the rate of heat build up on the image surface I of weld 12a can be used as an indicator of weld integrity because heat will be conducted from one portion of a sound weld to the image surface more rapidly than in a porous or disbonded weld. It has also been found that weld specimen 12a can be heated with a similar heat source not in contact with the specimen.

While the portable version of the apparatus 10 has been shown with a portable radiation source 29 mounted on top of scanner 11 a more preferred embodiment would use a remote radiation source 29A which is offset from scanner 11. Additionally, in a preferred mode of practicing the present invention, scanner 11 is also offset from the perpendicular when viewing the image side I of specimen 12. It has been found that heat from the operator's body will reflect off surface I and will be picked up by scanner 11 as a ghost image. Likewise, if scanner 11 is held at a 90° angle in relation to image surface I, a cold spot will be indicated on the resulting thermograph which is a reflection of the scanner itself. Therefore, both the radiation source 29 and scanner 11 should be offset somewhat from the perpendicular when inspecting specimen 12 in order to reduce the influence of reflected energy sources. In order to accomplish this preferred mode of practicing the present invention, remote and free standing radiation sources are generally used. It is also more expedient to use either semiportable or fixed energy source 29A because the amount of power required to operate the energy source requires the use of heavy cable therefore substantially eliminating the use of portable units.

It should be understood that the method of the present invention is applicable to subassemblies as well as fully assembled aircraft. It should also be understood that the method of the present invention is in fact applicable to any painted or unpainted metal surface, for example, petroleum storage tanks, hulls and bulkheads of ships or oil well drilling rigs, missile fuselages, etc. When used to inspect such structures as well as assembled aircraft, the apparatus not only includes the components previously discussed but might additionally include the components schematically described in FIG. 6. The apparatus includes a scanner assembly generally indicated at 60, which comprises an infrared scanner 61, a laser pointer 62 for visually marking scanner 61, a laser pointer 62 for visually marking the site viewed with a beam of light and a video camera 63 having auto focus and remote zoom capabilities to provide an operator with a video display of the image viewed by the scanner 61. Each of the components is compactly designed and individually, as well as removably mounted, to a platform 64 which is operatively associated with a pan and tilt arrangement 65 for remotely locating the scanner 61, pointer 62 and camera 63 as will be described more fully hereinafter.

Figure 6:
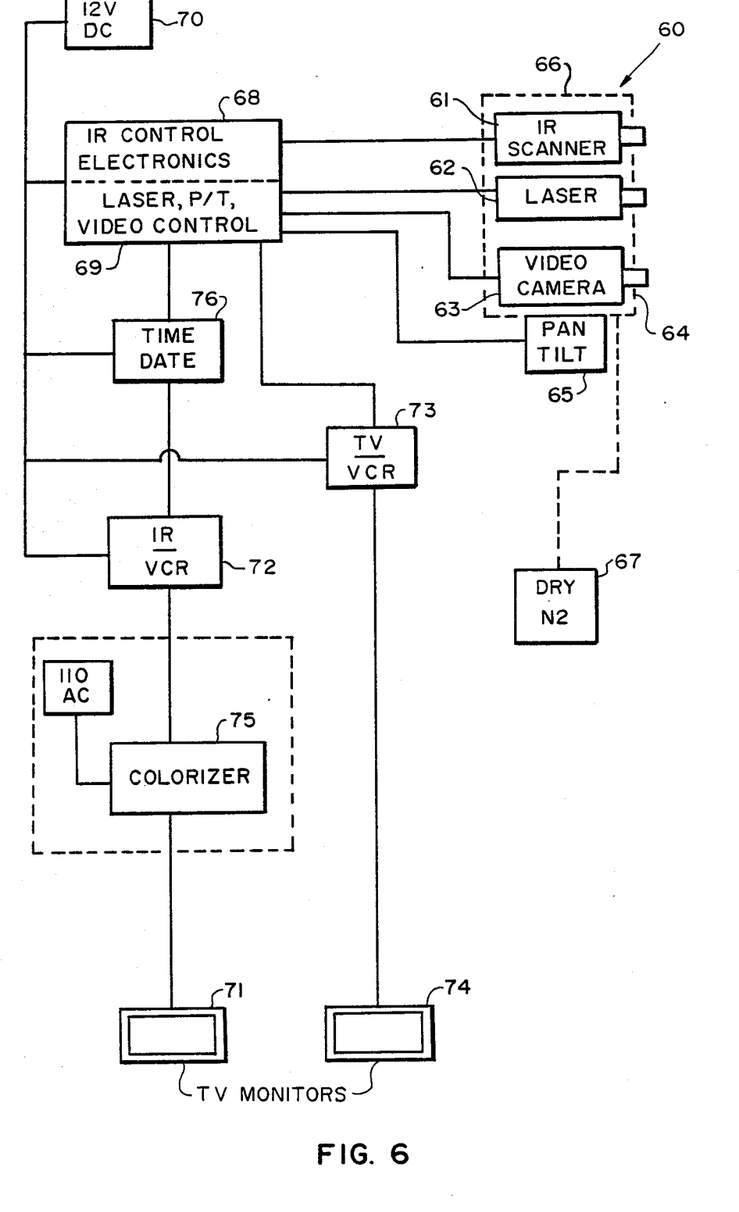
FIG. 6 is a schematic representation of still another configuration of the present invention.

When scanner 61 is used in a volatile, explosive or corrosive environment, such as, for example, a fuel tank, an optional enclosure 66 and dry nitrogen gas purge system 67 are provided to surround the electrical components of the apparatus with an atmosphere of substantially inert gas. This arrangement minimizes the possibility of explosion due to an electrical discharge or spark and thus render the equipment intrinsically safe. Additionally, this arrangement minimizes damage to the electrical equipment in the apparatus should the atmosphere of the inspection site be corrosive.

Remotely located from the scanning assembly 60 are the infrared scanner control-electronics unit 68 and the laser, pan and tilt video controls 69. A 12 volt D.C. battery 70 is used to power controls 68 and 69 when the apparatus is operated in the remote control mode. A date-time generator 76 provides a time and date of inspection which is displayed on monitor 71. Also included is an IR VCR 72 which provides a permanent record of the test display on monitor 71. A TV VCR 73 connected to a second monitor 74 provides a permanent record of the images viewed by camera 63 during the test procedure.

An optional colorizer 75 can be inserted between the IR VCR and monitor 71 in order to permit the operator to continuously observe temperature zones within the image, each color representing a different isotherm range. In lieu of a colorizer, a computer enhancement arrangement of the type manufactured by Interactive Video Corp. may be used and allows pictel by pictel analysis of the image with a sensitivity of approximately ±0.02° C. The computer enchancement arrangement provides analysis in real-time or alternatively, from a tape recording of the test using IR VCR 72. Thus, taping of the scanner signal to IR VCR 72 allows for later color enhancement or computer analysis, such later computer analysis being impossible if the signal is first recorded with color enhancement. In use, scanner 60 is located adjacent to a specimen being inspected.

In the practice of the present invention it has been found that both the rate of temperature increase (heat build up) on the image surface I or the rate of decay of heat applied to the image surface I can be used to evaluate the integrity of welds being inspected. The method used in the evaluation will generally be controlled by the type of thermal generator used and the point at which thermal energy is applied to a weld. If pulsed energy is applied to the image surface I generally the rate of decay is studied and if a contact heat source is used on the side of the specimen away from the scanner it is generally best to observe the rate of heat build up on the image surface of a weld.

Although the invention has been discussed and described with primary emphasis on one preferred embodiment, it should be obvious that adaptations and modifications can be made thereto without departing from the spirit and scope of the invention.

We claim:

1. A method of inspecting welds joining metal objects, said welds having a weld surface, comprising the steps of:
    (a) heating the welds by directing pulsating infrared radiation onto the weld surface so that the temperature of said welds is raised above ambient;
    (b) scanning the surface of said welds with a sensing device synchronously with the heating of the weld to detect and record any temperature differentials which might be present on the surface of said welds;

(c) sensing said temperature differentials and converting said temperature differentials into a signal representative of the intensity and location of said temperature differentials;

(d) transmitting said signal to a video display means; and (e) displaying the signal in real time on said video display means in the form of a thermal map of the weld surface, so that the quality of the welds may be determined.

2. The method of claim 1, wherein step (a) further comprises the steps of:

(a) providing a source of pulsating infrared radiation; and (b) irradiating the weld surface with said pulsating infrared radiation source so that the temperature of said welds is raised above ambient, the duration of the radiation pulse being set at a predetermined frequency and period relative to the thickness of said welds and the metal objects joined by said welds.

3. The method of claim 1, wherein step (b) further comprises the steps of:

(a) sensing the rate at which said welds cool by means of a radiometer sensitive to infrared radiation and;

(b) converting said cooling rate into an electrical signal representative of said cooling rate.

4. An emissivity independent method of inspecting welds joining metal objects, said welds having a surface, comprising the steps of:

(a) providing a source of pulsating infrared radiation having a first wave length;

(b) directing pulses of infrared radiation from said source onto the surface of said welds so that the temperature of said welds is raised above ambient;

(c) scanning the surface of said welds with an infrared radiation detecting device synchronously with the directing of pulses onto the surface for infrared radiation having a second wavelength to detect any temperature differentials which might occur on said surface as a result of the exposure of said surface to said pulses of infrared radiation; and (d) converting any detected temperature differentials into usable signals and displaying the same on a video display means in the form of a thermal map of said surface, so that the quality of the welds may be determined.

5. The method of claim 4, wherein step (b) comprises:

(a) directing pulses of infrared radiation having a first wavelength onto the surface of welds joining metal objects; and (b) adapting the frequency and duration of said radiation pulses to the thermal conductivity and thickness of said welds whereby heat is conducted away from said welds at a rate which is less than the rate at which radiant energy is directed upon said welds.

6. The method of claim 4, wherein step (c) comprises scanning the welds with an infrared detector to measure temperature differentials occurring on said welds and which are characterized by infrared radiation of a second wave length emitted from said surface during the interval between said pulses of radiation.

7. The method of claim 4, wherein step (b) comprises:

(a) directing pulses of infrared radiation having a first wavelength onto the surface of welds joining metal objects; and (b) adapting the frequency and duration of said radiation pulses to the thermal conductivity and thickness of the weld whereby after the temperature is raised above its normal ambient, heat is conducted away from the weld surface at a rate which is greater than the rate at which thermal energy is applied to the weld surface.

8. An apparatus for the non-destructive, real time evaluation of welds, each weld having a weld surface, comprising in combination:

(a) thermal energy means for directing pulsating infrared radiation onto the weld surface so that the temperature of the welds is raised above ambient;

(b) means for scanning the surface for infrared radiation being emitted therefrom synchronously with the operation of the thermal energy means directing pulsating infrared radiation onto the weld surface including means for capturing said emitted radiation;

(c) means for converting said captured radiation into a signal representative of the thermo-physical characteristics of said weld; and (d) means for visually displaying said signal in a form suitable for interpretation of said signal so that the quality of the welds may be determined.

9. The apparatus of claim 8, wherein said thermal energy means comprises source means for generating infrared radiation of a first wave length and pulsing means for interrupting the infrared radiation being emitted from said source means whereby said infrared radiation is directed upon the weld in pulses of varying frequency and duration along a radiation path.

10. The apparatus of claim 8, wherein said means for scanning the weld surface comprises a scanning camera means capable of detecting and capturing infrared radiation, said camera means further including electro-optical transducer means for converting said radiation into an electrical signal.

11. The apparatus of claim 10, wherein said means for converting said captured radiation into a signal comprises signal processor means for converting said electrical signal into a video compatible signal representative of the thermophysical characteristics of said weld.

12. The apparatus of claim 8, wherein said means for visually displaying said signal comprises a video monitor means.

13. The apparatus of claim 12, wherein said means for visually displaying said signal comprises in combination a video tape recording means and said video monitor means.

14. The apparatus of claim 13, wherein said video monitor means comprises color video monitor means.

15. The apparatus of claim 9, wherein the wavelength of said infrared radiation is from about 0.5 to about 2.5 microns.

16. The apparatus of claim 10 wherein said infrared radiation has a wavelength of about 8 to about 12 microns.

17. The apparatus of claim 9, wherein said pulsing means comprises shutter means for alternately closing and opening the path of radiation between said infrared source and said weld at a desired frequency.

18. The apparatus of claim 9, wherein said pulsing means comprises electronic means for interrupting a flow of energy to said infrared source means in a periodic manner and at a desired frequency.

19. The apparatus of claim 8, wherein said thermal energy means further includes means for varying the intensity of the thermal energy produced by said thermal energy means.

* * * * *